United States Patent [19]
Gibbs

[11] Patent Number: 6,134,294
[45] Date of Patent: Oct. 17, 2000

[54] DEVICE AND METHOD FOR PRECISION MACULAR X-IRRADIATION

[75] Inventor: Frederic A Gibbs, Salt Lake City, Utah

[73] Assignee: University of Utah Research Foundation, Salt Lake City, Utah

[21] Appl. No.: 09/023,827

[22] Filed: Feb. 13, 1998

[51] Int. Cl.[7] ........................................................ A61N 5/10
[52] U.S. Cl. ................................ 378/65; 378/69; 378/206
[58] Field of Search .................................... 375/65, 64, 68, 375/69, 205, 206; 606/12, 130

[56] References Cited

U.S. PATENT DOCUMENTS

| | | | |
|---|---|---|---|
| 5,080,100 | 1/1992 | Trotel | 378/206 |
| 5,354,314 | 10/1994 | Hardy et al. | 606/130 |
| 5,553,112 | 9/1996 | Hardy et al. | 378/206 |
| 5,624,437 | 4/1997 | Freeman et al. | 606/12 |

OTHER PUBLICATIONS

Berson et al., Radiotherapy for Age–related Macular Degeneration: Preliminary Results of a Potentially New Treatment, Int. J. Radiation Oncology Biol. Phys., vol. 36, No. 4, pp. 861–865, 1996.

Akmansu et al., External Radiotherapy in Macular Degeneration: Our Technique, Dosimetric Calculation, and Preliminary Results, Int. J. Rad Oncology Bio. Phys., vol. 40, No. 4, pp. 923–927, 1998.

Freire et al., External Radiotherapy in Macular Degerneration: Technique and Preliminary Subjective Response, Int. J. Radiation Oncology Biol. Phys., vol. 36, No. 4, pp. 857–860, 1996.

Brady et al., Radiation Therapy for Macular Degeneration: Technical Considerations and Preliminary Results, Int. J. Radiation Oncology Biol. Phys., vol. 39, No. 4, pp.945–948, 1997.

*Primary Examiner*—David P. Porta
*Attorney, Agent, or Firm*—Terry M. Crellan

[57] ABSTRACT

A device for precision X-irradiation of the macular region of the retina of a patient's eye has a mounting plate mounted to a linear accelerator collimator. A housing extends from the mounting plate, and a secondary collimator is positioned in the housing. An elongate aperture extends through the secondary collimator and is in linear alignment with an axis of an X-ray beam emanating from the linear accelerator collimator. A support member extends outwardly from a side of the housing, and an elongate, hollow, sight tube is mounted on the support member. The longitudinal axis of the sight tube aligns with the axis of the X-ray beam so that the axis of the sight tube and the axis of the X-ray beam intersect each other. A light beam is transmitted down the sight tube. The light beam impinges on a cornea of a patient's eye. Light reflected from the cornea is transmitted up the sight tube so that impingement of the light beam on the cornea can be observed through an upper end of the sight tube. The patient is positioned so that the macular region of the retina of the patient's eye lies at the intersection of the longitudinal axis of the sight tube and the axis of the X-ray beam.

8 Claims, 3 Drawing Sheets

DEVICE AND METHOD FOR PRECISION MACULAR X-IRRADIATION

BACKGROUND OF THE INVENTION

1. Field of the Invention

The present invention relates generally to treatment of age-related macular degeneration. In particular, the present invention relates to apparatus and method for X-irradiation of the macular region of the retina.

2. State of the Art

In recent years there has been a multitude of developments in the treatment of age-related macular degeneration. Macular degeneration is the leading cause of visual loss in those over the age of 50. There have been methods proposed that utilize medication, laser treatment and radiotherapy. Unfortunately, an acceptable standard treatment of this condition has not been developed. In a number of trials, retinal radiotherapy has resulted in stabilized or improved visual acuity in the majority of patients in short term follow-up with no reported significant toxicity. However, it is assumed and accepted by those skilled in this area that it is unnecessary, and potentially deleterious, to irradiate the entire retina. Those trials involving radiotherapy have been limited by the apparatus and methods presently available to the irradiation of the entire retina. It would be highly desirable to have available apparatus and methods of treating macular degeneration with radiotherapy in which irradiation is essentially limited to the macula. Such apparatus would permit precision X-irradiation of the macular region of the retina using smaller radiation fields than have been heretofore possible.

OBJECTIVES AND BRIEF DESCRIPTION OF THE INVENTION

A principal objective of the invention is to provide novel apparatus for X-irradiation of the macular region of the retina wherein the radiation fields are centered on and substantially limited to the macula, and wherein irradiation of the remainder of the retina and incidental irradiation of the lens, the cornea and the optic nerve of the eye are limited to a minimum, low level dose.

A further objective of the present invention is to provide novel apparatus having multiple conically oriented beam positions to minimize irradiation of the lens of the eye and other normal tissue, with the beam being directed through an extended collimator to minimize beam penumbra, and further wherein the collimator has an elliptical aperture that creates a circular beam image at the angle of incidence on the retina.

A still further objective of the present invention is to provide novel apparatus that incorporates a video system that enables precise alignment of the radiation beam with the macula of the eye and real-time monitoring of the position of the eye during treatment, with an electronic means further being provided to define the center of the target with respect to the actual beam image so as to overcome any inherent lack of mechanical isocentricity of the linear accelerator and associated apparatus.

An additional objective of the present invention is to provide novel apparatus having a system for positioning the patient's head in the x, y and z directions, where by the patient's eye can be properly positioned and the position can be monitored and adjusted before and during treatment.

Another objective of the present invention is to provide a novel method for making a thick lead-alloy collimator that has an elliptical aperture as small as 5 to 6 mm.

The above objectives are achieved in accordance with the present invention by providing a device for precision macular X-irradiation is directed to and essentially limited to the macular region of the retina. The device comprises a mounting plate that is mounted to a linear accelerator collimator. The mounting plate has a housing extending therefrom in which an extended cerrobend (lead alloy) secondary collimator is positioned so that the elongate aperture extending through the secondary collimator is in linear alignment with an X-ray beam from the linear accelerator collimator.

A side mounted support member is attached to the housing so that the support extends outwardly from the side of the housing. An elongate, hollow, sight tube is mounted on the support member such that the sight tube is disposed in a vertical orientation when the mounting plate of the device is mounted to a linear accelerator collimator. In a preferred embodiment of the device, the sight tube is mounted on the support member so that the sight tube can be rotated about its longitudinal axis. In addition, means are provided for insuring that the longitudinal axis of the sight tube aligns with the axis of the X-ray beam from the secondary collimator so that the axis of the sight tube and the X-ray beam intersect each other.

A light beam is transmitted down the sight tube substantially along the longitudinal axis of the light tube. Reflected light is transmitted up the sight tube from the cornea so that the impingement of the light beam on the cornea can be observed through the upper end of the sight tube. A first video camera is positioned at the upper end of the sight tube for viewing through the sight tube. The first camera is used to insure the intersection of the axis of the sight tube and the X-ray beam and to monitor and adjust the patient's eye position. A second video camera is positioned outwardly and downwardly from the lower end of the sight tube and at 90 degrees to it. The second camera is used to properly position the patient's cornea so that the retina (at known distance from the cornea) lies at the plane of intersection of the sight tube and X-ray beam.

The two cameras and the sight tube can be rotated as a unit about the longitudinal axis of the sight tube. The treatment couch on which the patient lies also rotates so that the patient while lying supine rotates about a vertical axis through the macular region of the patient's eye. This allows the X-ray beam from the secondary collimator to be directed on the macular region of the patient's eye in a series of conically coincident beams that pass by the lens of the patient's eye and impinge on the macular region of the eye as the patient is rotated beneath the lower end of the sight tube. It has been found advantageous to rotate the patient so that the patient's eye makes from one to five equal angular movements from its initial position. X-ray beams are directed at the macular region of the patient's retina during the initial position and each of the subsequent positions following an angular movement of the eye. This produces a series of separate, conically oriented beams that are directed to the macular region of the retina, with the beams being equally spaced from each other. It should be recognized, however, that the device of the present invention is useful even without the rotation of the patient. A single irradiation of the macular region is better than no treatment, but it is recognized that dose uniformity is improved with two conically coincident directions on the same plane and normal tissue sparing is further enhanced with the conical array.

It is also recognized that it is theoretically possible to rotate the patient in a continuous angular movement, with irradiation being performed continuously during the rotation of the patient. However, the apparatus for rotating the patient would have to be elaborately designed to accomplish a rather rapid rotation while maintaining the eye of the patient centered about the vertical axis through the sight tube. It is preferred to rotate the patient in discreet movements as described above. The apparatus for rotating the patient in discreet, separate motions is greatly simplified and more importantly, the operator can adjust the direction of the X-ray beam for each step to counteract any lack of mechanical isocentricity of the linear accelerator and the attached device of the present invention. It is also easier for the patient to fixate on the visual target for brief discrete intervals.

It should also be recognized that the sight tube and the two cameras need not rotate. It is sufficient to rotate the patient without concurrent rotation of the sight tube and camera system. However, it is advantageous to rotate the sight tube and camera system simultaneously with the patient to provide the operator of the device with a consistent visual view of the patient's eye. By rotating the camera system concurrently with the patient, the operator maintains the same view and perspective of the eye throughout the procedure, thus greatly facilitating any positional adjustments required.

Additional objects and features of the invention will become apparent from the following detailed description, taken together with the accompanying drawings.

THE DRAWINGS

Preferred embodiments of the present invention representing the best mode presently contemplated of carrying out the invention are illustrated in the accompanying drawings in which.

DETAILED DESCRIPTION OF THE ILLUSTRATED EMBODIMENTS

Figure 1:
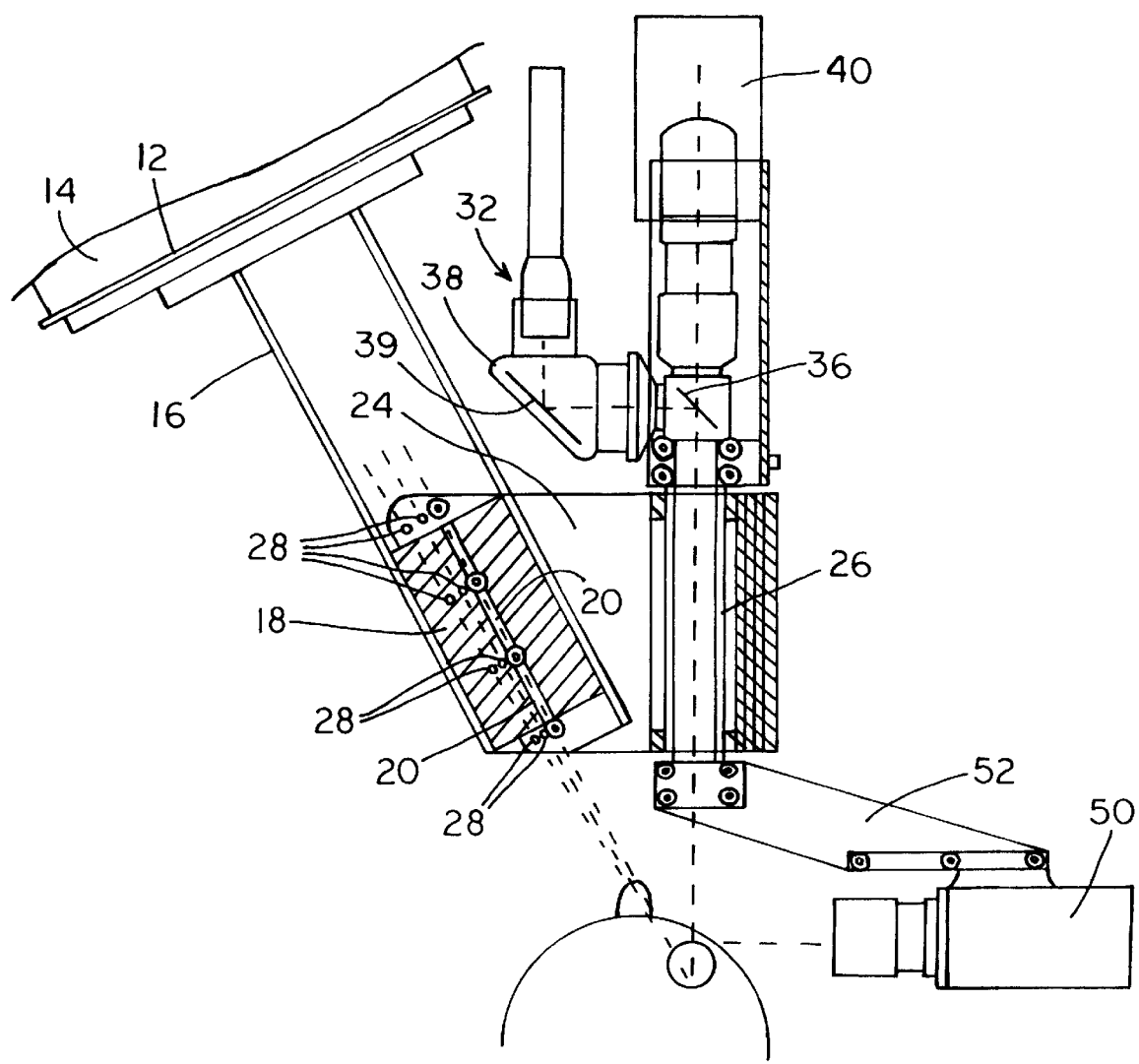
FIG. 1 is a elevational view of a device in accordance with the present invention for precision X-irradiation of the macular region of an eye of a person in the treatment of the eye for macular degeneration.

Referring now to the drawings, a preferred embodiment of the device of the present invention is shown. The device comprises a plate 12 that mounts to a linear accelerator collimator 14. The linear accelerator collimator 14 is well known apparatus and needs no further description. The device of the present invention is supported entirely from the linear accelerator collimator 14 by the mounting plate 12.

A housing 16 which is preferably circular in cross-sectional shape extends downwardly at a substantially right angle from the mounting plate 12. The longitudinal axis of the housing 16 is positioned to be coaxial with the axis of the X-ray beam 22 from the linear accelerator collimator 14.

A secondary lead alloy collimator 18 is positioned in the lower portion of the housing 16. The secondary lead alloy collimator 18 has an outer perimeter that fits snugly within the housing 16. Thus, for a housing 16 that has a circular cross-sectional shape, the secondary collimator 18 is cylindrical in shape having a circular cross-sectional perimeter. An elongate, elliptically-shaped passage 20 extends from one end of the secondary collimator 18 to the other end along the central axis of the secondary collimator 18. The axis of the elliptically-shaped passage 20 is oriented so as to be coaxial with the central axis of the secondary collimator 18 and thus also coaxial with the X-ray beam 22 from the linear accelerator collimator 14.

The secondary collimator 18 will generally have a length of from about 15 cm to 25 cm or more and a cross-sectional thickness of about 10 cm to 14 cm and preferably about 12 cm. The elliptical passage 20 has a cross-sectional dimension of about 5 mm ×6 mm, but optimal size determination requires further clinical testing. The axis of the X-ray beam from the linear accelerator collimator 14 will make an axis of about 28 degrees to 32 degrees from the vertical. The elliptical shape of the passage 20 shapes the X-ray beam 22 from the linear accelerator collimator 14 so that when the beam 22 impinges on the retina of the eye of a patient, the image cast on the retina will be generally circular in shape. The extended length of the secondary collimator 18 minimizes beam penumbra so as to minimize incidental irradiation to the retina outside of the area of the main image that is cast on the retina by the beam.

Figure 2:
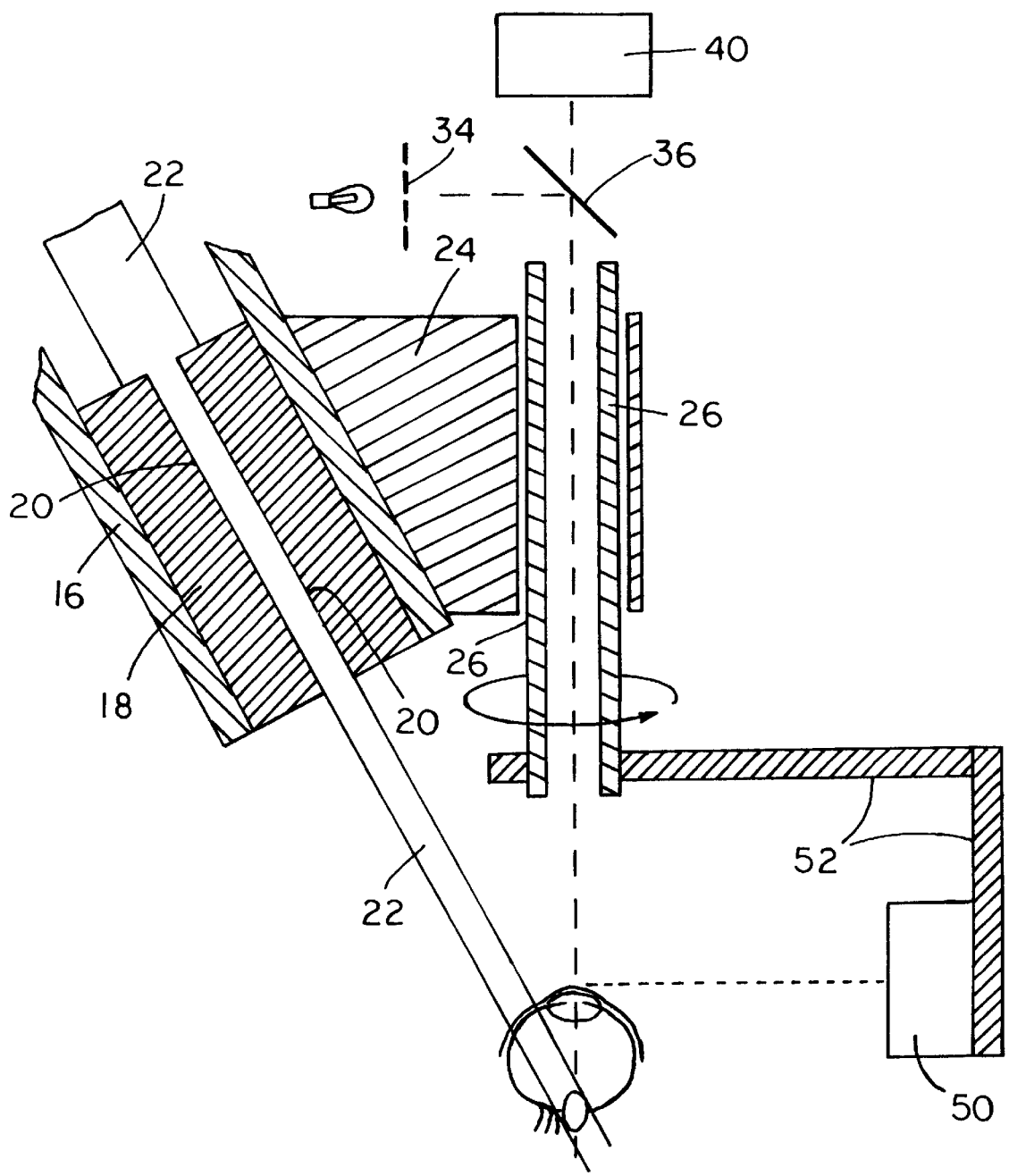
FIG. 2 is a diagrammatic, representation in vertical cross section showing the major components of the device of FIG. 1 in block form.

A support member 24 is attached to the housing 16 so as to extend outwardly from the housing 16. An elongate, hollow, sight tube 26 is mounted on the support member 24 so that the sight tube 26 is oriented essentially vertical when the mounting plate 12 of the device is mounted to the linear accelerator collimator 14. To accommodate larger elliptical apertures 20, the support member 24 has means for adjusting to the particular angle that X-ray beam from that linear accelerator collimator 14 makes with the vertical and still allow the X-ray beam to miss the lens of the eye. As mentioned above, it is common for the X-ray beam from a linear accelerator collimator 14 to make an angle of 28, 30 and 32 degrees with vertical. The means on the support member 24 for adjusting to these angles is advantageously a series of openings 28 in the support member 24 by which the support member 24 is attached by bolts to the housing 16. As shown diagrammatically by circular line 30 in FIG. 2, in the preferred embodiment of the invention, the sight tube 26 is mounted so that it can be rotated about its longitudinal axis. However, it should be recognized that providing for rotational motion of the sight tube 26 is only a preferred embodiment. As stated previously, it is not essential that the sight tube 26 have the capability of rotating about its axis.

Means are provided for transmitting a directional light beam down the sight tube 26. As shown diagrammatically in FIG. 2, a light source shines a light beam through a target shaped aperture 34 with a point light source at its center. The light from this light source is directed down the sight tube 26 along the longitudinal axis of the light tube 26 by a plate beam splitter 36. As shown in FIG. 1, the light source 32, which incorporates the small aperture 34 therein, is positioned alongside the sight tube 26, and an optical element 38 containing a mirror 39 directs the beam of light to the plate beam splitter 36 in the sight tube 26.

When the device of the present invention is attached to the linear accelerator collimator 14, the X-ray beam 22 from the secondary collimator will intersect the vertical axis of the sight tube. It is an object of the device of the present invention to locate this intersection precisely at the macular region of the eye of a patient being treated for macular degeneration.

A video camera 40 is mounted to the upper end of the sight tube 26 for viewing through the sight tube 26. Reflected light is transmitted up the sight tube 26 from the cornea of the patient's eye when the patient's eye is positioned in alignment with the longitudinal axis of the sight tube 26. The reflected light is produced by the impingement of the light beam which is transmitted down the sight tube 26 onto the cornea. The reflected light travels back up the sight tube 26 and is allowed to pass by the plate beam splitter 36 so that the reflected light can be viewed by the camera 40.

The appropriate position of the patient's eye and the reflection of the light from the cornea with respect to the longitudinal axis of the sight tube is determined by fundus camera examination by an ophthalmologist of the eye to be treated. With the patient staring at a target coaxial with his view of the macula, the ophthalmologist can picture how the landmarks of the iris and the light reflection from the cornea should relate to the central target point on the macula. This surrogate target point relative to the corneal reflection and iris landmarks becomes the effective target point for the treatment.

Inasmuch as the X-ray beam from the secondary collimator 18 intersects the central axis of the sight tube 26, the X-ray beam can be made to impinge precisely on the macular region of the patient's eye by positioning the patient so that the macular region of the eye is in vertical alignment with the central axis of the sight tube 26 and at a precise distance downwardly from the sight tube 26.

To position the patient so that the eye to be treated is in alignment with the central axis of the sight tube 26, the patient is positioned on a couch so as to lie supine with the eye of the patient looking vertically upward. The position of the patient is adjusted in the x, y and z coordinates so that vertical axis of the target point is positioned relative to the corneal reflection as determined by the ophthalmologist. This is done by having the patient stare at the point of light that is being transmitted down the sight tube. The patient is then positioned by moving the couch on which the patient lies until the point of reflected light is seen in its correct position in camera 40.

Although the treatment couch of any medical linear accelerator can be adjusted in these axes, the adjustment lacks the necessary precision. Also, these adjustments must be made by the operator from a remote position outside the radiation shielding vault under video control. Since the device is situated only a few centimeters from the patient's face, fine control is critical. In principle, these motions could be accomplished by a separate 3-dimensional x, y and z linear motion table under the patient's head. A less costly solution, a tilt-table controlled by stepper motors operation three triangularly positioned screw jacks, has been used in this device. Since the angular deviation of the eye from the vertical axis is small and it remains fixated on the light target, the effects of a linear motion table or a tilt table become practically indistinguishable since the tilt table motors can be differentially turned so as to affect discrete x, y and z motions of the eye. However, this application does not depend on these specific means of positioning the patient's eye.

In the preferred use of the device of the present invention, the patient is rotated so that several distinct beams of X-rays impinge on the retina. These beams are conically oriented to minimize irradiation of the lens and other normal tissue of the eye. Experience has shown that mechanical error in coincident alignment of the X-ray beam 22 and central axis of the sight tube 26 can not be reduced much below 1 mm.

Thus, as the patient is rotated from one position to another, it is not realistically possible to make the X-ray beam 22 and central axis of the sight tube 26 remain mechanically aligned for each position to which the patient is rotated. According to the invention, an electronic means of superimposing a target reticle on the image of the eye on the video monitor is provided. This enables the center of the radiation beam to be defined electronically for each of the treatment positions. For large corrections, problems with parallax would be anticipated. However, since the mechanical accuracy is within plus or minus 0.5 mm, the electronic correction required to eliminate the error due to lack of isocentricity will be less than plus or minus 0.4 degree as viewed from the target light source. This is too small of an angular correction to require further geometric correction.

Figure 3:
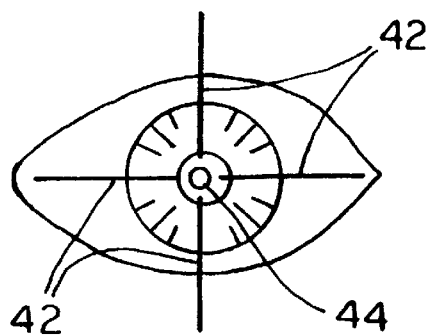
FIG. 3 is a view through the first camera of the device of FIG. 1, i.e., the camera mounted at the top of the device.

Target cross hairs 42 are electronically computer generated to appear in camera 40 as shown in FIG. 3. These cross hairs 42 can be remotely adjusted. During calibration of the device, a fluorescent plate is used instead of the eye of an actual patient. The image of the actual x-ray beam 22 can be viewed on the fluorescent plate. The cross-hairs 42 are electronically centered on the image of the X-ray beam 22, and these positions of the cross-hairs 42 are stored in memory for each of the rotational positions that will be used when treating an eye of an actual patient. During subsequent actual treatment of a patient, the patient is rotated to the desired positions, and in each position the cross-hair 42 stored in memory for that position is recalled from computer memory, and the recalled cross-hair 42 is used to position the point of light 44 of the reflected beam seen in the camera 40 at the cross of the cross-hairs 42 as shown in FIG. 3.

Coincidence of the central axis of the sight tube and the X-ray beam are thus accomplished in each position of the rotation of the patient by use of the cross-hairs 42 and camera 40. To precisely position the intersection of the X-ray beam 22 at the macular region of the eye of the patient, a second camera 50 is used. The second camera 50 is preferably a video camera. The second camera 50 is mounted on an arm 52 that extends outwardly and downwardly form the lower end of the sight tube 26. The second camera 50 is positioned a precisely set distance downwardly from the end of the sight tube 26, and the second camera 50 is aimed at the cornea of the eye of the patient.

Figure 4:
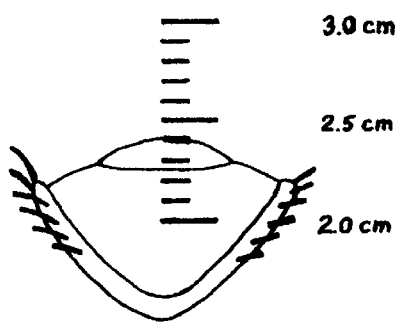
FIG. 4 is a view through the second camera of the device of FIG. 1, i.e., the camera mounted at the bottom of the device.

A scale is electronically computer generated in the second camera 50 as shown in FIG. 4. The scale is marked in distances from the intersection of the central axis of the sight tube 26 and the X-ray beam 22. Inasmuch as it is this intersection that is desired to be located at the retina, the patient is then moved in the vertical direction either up or down until the upper surface of the cornea is located at the marking on the scale which has previously been determine by ultrasound as being the actual distance from the cornea to the retina of the eye being treated.

Figure 5:
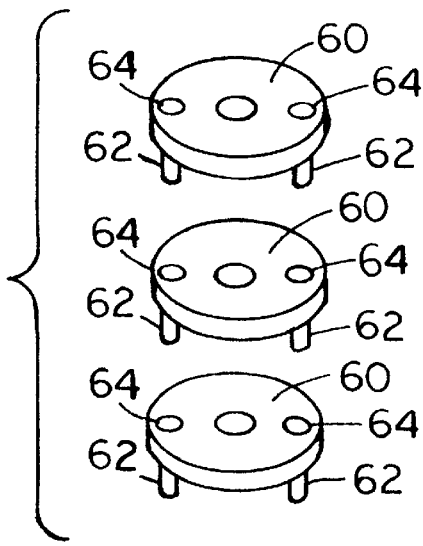
FIG. 5 is a pictorial representation of the secondary collimator of the device of the present invention, showing how the secondary collimator is made of a plurality of lead alloy disks which are stacked together.

In a related aspect of the invention, a method is disclosed for making the elongate, secondary, lead alloy collimator 18. An elliptical aperture must be formed in the elongate, lead alloy collimator 18, and the elliptical aperture must be as small as 5 to 6 mm. The novel process for making the elongate, lead alloy collimator 18 is to form it as a plurality of relatively thin discs 60. FIG. 5, is an exploded pictorial of three out of many discs 60 that are used to form the elongate, lead alloy collimator 18.

Each disc 60 is flat and has a thickness of about 0.35 to 0.6 inch, preferably about 0.5 inch. One surface of each disc 60 has a pair of diametrically opposite projections 62 that extend slightly from the flat surface of the disc. The other surface of each disc 60 has a corresponding pair of indentations 64 that are coaxial with respective projections 62 on the first side of the disc 60. The projections 62 of one disc 60 are received in corresponding indentations 64 of an adjoining disc 60 to maintain proper orientation of the elliptical apertures in each of the discs 60.

The discs 60 are cast from molten lead alloy in molds that have a cavity which is substantially circular perimeter. The mold incorporates an elliptically machined pin in the center of the mold. When molten lead alloy hardens in the mold, the elliptically machined pin is pulled and extracted from the disc 60 that has been cast in the mold. The mold also incorporates means for forming the projections 62 and indentations 64 in opposite flat faces of the discs 60 as the discs are molded. The elliptically machined pin is carefully oriented and positioned so that when the discs 60 are assembled together, the elliptical apertures in the discs are in proper registration and orientation to form the elongate, elliptical opening 20 thought the elongate, lead alloy collimator 18.

Multiple discs 60 are cast and stacked together using the projections 62 and indentations 64 to create proper alignment of the apertures in the stacked discs as mentioned above. The stacked discs are then soldered together to create the elongate, secondary, lead alloy collimator 18.

Although preferred embodiments of the present invention have been illustrated and described, it is to be understood that the present disclosure is made by way of example and that various other embodiments are possible without departing from the subject matter coming within the scope of the following claims, which subject matter is regarded as the invention.

What is claimed is:

1. A device for precision X-irradiation of the macular region of the retina of a patient's eye, said device comprising
    a mounting plate which is mounted to a linear accelerator collimator;
    a housing extending from said mounting plate;
    a secondary collimator positioned in said housing;
    an elongate aperture extending through said secondary collimator, said elongate aperture being in linear alignment with an axis of an X-ray beam emanating from the linear accelerator collimator;
    a support member attached to said housing so that said support member extends outwardly from a side of said housing;
    an elongate, hollow, sight tube mounted on said support member so that said sight tube is disposed in a substantially vertical orientation;
    means for aligning a longitudinal axis of said sight tube with respect to the axis of the X-ray beam emanating from the linear accelerator collimator so that the axis of the sight tube and the axis of the X-ray beam intersect each other;
    means for transmitting a light beam down said sight tube substantially along the longitudinal axis of the light tube so that said light beam impinges on a cornea of a patient's eye when the patient looks into a bottom end of said light tube and stares directly at a point from which said light beam is being transmitted down said light tube, whereby reflected light is reflected from the cornea of the patient's eye and is transmitted up the sight tube so that impingement of the light beam on the cornea can be observed through an upper end of said sight tube; and
    means for positioning the cornea of the patient's eye so that the macular region of the retina of the patient's eye lies at the intersection of the longitudinal axis of the sight tube and the axis of the X-ray beam.

2. A device in accordance with claim 1 wherein the elongate aperture in said secondary collimator is elliptical in shape.

3. A device in accordance with claim 1 wherein said sight tube is mounted on said support member so that said sight tube can be rotated about its longitudinal axis.

4. A device in accordance with claim 1 further comprising a video camera positioned at the upper end of said sight tube for viewing through said sight tube.

5. A device in accordance with claim 4 wherein said means for positioning the cornea of the patient comprises
    a second video camera positioned outwardly and downwardly from the lower end of said sight tube, with said second video camera being aimed in a direction that intersects said longitudinal axis of said sight tube and is substantially perpendicular to said longitudinal axis of said sight tube so that an upper surface of the cornea of the patient is visible in the view of said second video camera and the patient an be moved to position the upper surface of the cornea at a desired position relative to the lower end of said sight tube.

6. A method of X-irradiation of the macular region of the retina of a patient's eye, said method comprising
    positioning a patient in a supine position, with the patient's eye staring at a point substantially vertically upward from the macular region of the retina of the patient's eye;
    directing an X-ray beam on the macular region of the retina, with the X-ray beam being projected downwardly through the eye of the patient so that the X-ray beam makes a sufficient angle to vertical such that the X-ray beam does not impinge on the lens of the eye of the patient;
    rotating the patient about a vertical axis through the macular region of the patient's eye; and
    allowing the X-ray beam to be directed into the patient's eye at least at two different positions during the rotation of the patient.

7. A method in accordance with claim 6 wherein the patient is rotated in up to six different rotational positions and the X-ray beam is directed into the patient's eye at each of the different rotational positions.

8. A method in accordance with claim 6 wherein the patient is rotated in one complete rotation, and the X-ray beam is directed into the patient's eye continuously during the rotational movement of the patient.

\* \* \* \* \*